United States Patent [19]

Stenzel et al.

[11] 4,146,792

[45] Mar. 27, 1979

[54] PAPER SECURED AGAINST FORGERY AND DEVICE FOR CHECKING THE AUTHENTICITY OF SUCH PAPERS

[75] Inventors: Gerhard Stenzel; Erhard Lehle, both of Munich, Fed. Rep. of Germany

[73] Assignee: G.A.O. Gesellschaft fur Automation und Organisation mbH, Fed. Rep. of Germany

[21] Appl. No.: 883,592

[22] Filed: Mar. 6, 1978

Related U.S. Application Data

[63] Continuation of Ser. No. 725,146, Sep. 20, 1976, abandoned, which is a continuation-in-part of Ser. No. 352,051, Apr. 16, 1973, abandoned.

[30] Foreign Application Priority Data

May 8, 1973 [AT] Austria .................................. 3824/73

[51] Int. Cl.² ............................. G01J 1/42; G01J 1/58
[52] U.S. Cl. .................................... 250/365; 250/372; 250/483
[58] Field of Search ................ 283/8 B; 250/372, 271, 250/365, 483; 427/7

[56] References Cited

U.S. PATENT DOCUMENTS

| 2,255,696 | 9/1941 | Clifford | 283/8 B |
| 2,262,492 | 11/1941 | Farrell | 283/8 B |
| 2,538,784 | 1/1951 | Kantrowitz | 427/7 |
| 3,473,027 | 10/1969 | Freeman | 250/365 |
| 3,663,813 | 5/1972 | Shaw | 250/271 |

OTHER PUBLICATIONS

Fluorescent and Other Gaseous Discharge Lamps by Forsythe & Adams, 1949, pp. 47–50.

*Primary Examiner*—Harold A. Dixon
*Attorney, Agent, or Firm*—McGlew and Tuttle

[57] ABSTRACT

The paper carries, at one or more points, materials which, in the excited condition, fluoresce in the visible, ultraviolet, or infra-red spectral range in the characteristic emission spectra. The device includes a light source for exciting fluorescent substances, a condenser lens concentrating the light emitted by the paper, a narrow band interference filter, a focusing lens, and a series of photocells arranged in the focal plane of the focusing lens. The geometric arrangement of the photocells is chosen appropriately to identify an emission-line doublet. The outputs of the photocells are fed to a pre-amplifier and then to a comparator which may effect a subtraction of the amplified photocell output to provide an output signal. In a variation, the quotient of the photocurrents of two photocells is compared to establish the authenticity of the paper.

9 Claims, 5 Drawing Figures

PAPER SECURED AGAINST FORGERY AND DEVICE FOR CHECKING THE AUTHENTICITY OF SUCH PAPERS

CROSS-REFERENCE TO RELATED APPLICATION

This application is a continuation of application Ser. No. 725,146 filed Sept. 20, 1976 which is a continuation in part of application Ser. No. 352,051 filed Apr. 16, 1973, both now abandoned.

FIELD AND BACKGROUND OF THE INVENTION

This invention relates to a paper secured against forgery and to a device for checking the authenticity of such papers. By the term "paper", there are to be understood all papers or other information carriers representing an ideal value independently of their material value, and whose imitation, by unauthorized persons, must be rendered as difficult as possible. In this sense, "papers" as used herein, are bank notes, shares, checks, deeds, identity cards, credit cards, contracts, and even works of art.

In order to make papers safe against forgery, it is known to provide, in the paper, safety features, such as safety threads, water marks and the like, with care being taken that any imitation of the safety features is possible only at a high cost, that is, at a cost which is higher than the ideal value represented by the paper.

However, as the many forgeries, particularly of bank notes, show, it has clearly been impossible so far to afford satisfactory safety against forgery. An investigation of the known methods and measures for securing paper against forgery has shown that, in general, these known methods and measures are relatively easy to detect, by the forger, on the paper itself, and thus are relatively easy to imitate.

SUMMARY OF THE INVENTION

The invention is based on the recognition that safety against authorized imitation can be substantially increased if there can be provided, in the paper, safety features which require not only a high technical expense but also a high scientific expense to be analyzed. Furthermore, such authenticity features should be based on substances which, after any successful analysis, can be reproduced only at a high expense. To this end, the substances must not be commercially available either, so that the safety features are not rendered valueless by disclosure.

In accordance with the invention, a solution is proposed which takes the above recognitions and conditions into account. The underlying concept of the present invention is the provision of fluorescent materials of a particular concentration as safety features on the entire paper or at one or more points thereof, and which materials, in the excited condition, fluoresce in the visible, ultraviolet, or infra-red spectral range in characteristic emission spectra. Such characteristic emission spectra permit an unambiguous identification of these substances and of any mixtures thereof. Since many of these substances are colorless, they cannot be perceived with the naked eye, so that the marked points cannot be recognized readily.

For rendering any forgery even more difficult, a mixture of several substances, fluorescing within narrow spectral bands, are advantageously provided on or in the paper, so that the mixture ratio affords additional safety.

For the same reason, it is further possible to mix the substances used for the authenticity check with further fluorescent substances which emit light within narrow spectral ranges outside the wave length range examined by the checking device. This does not affect the identification of the substances used for the authenticity check, but a forger will encounter difficulties because he cannot readily recognize which substances are evaluated in the authenticity check.

It is further possible to add fluorescent substances emitting light within broad spectral bands, even if these do not emit light in the spectral band examined in the authenticity checked. However, the visual impression of the fluorescent color can be changed completely by adding fluorescent paints emitting light within broad spectral bands.

An outstanding advantage of the invention is that the authenticity of papers can be quickly and reliably established by an automatic checking device, for example, in automatic money changers or vending machines, during money transactions at bank counters, when checking identity cards, etc.

For an understanding of the principles of the invention, reference is made to the following description of typical embodiments thereof as illustrated in the accompanying drawings.

DESCRIPTION OF THE PREFERRED EMBODIMENTS

As previously mentioned, the protection of the papers against forgery is effected by providing the papers with fluorescent materials of a particular concentration, either on the entire paper or at one or more points thereof, these fluorescent materials, in the excited condition, fluorescing in the visible, ultraviolet or infra-red spectral range in characteristic emission spectra. The fluorescent materials may be provided in the form of a die stamping ink, or else the paper may be impregnated with the fluorescent material.

As an example of the fluorescent material, there may be used three yellow security coloring substances which contain a common broad-band fluorescing pigment and respective different narrow-band fluorescent materials. The three coloring substances, obtained as will be described, appear yellow to the observer in daylight and yellow-green to the observer under ultraviolet radiation. Visually, the coloring substances cannot be distinguished, either in daylight or under ultraviolet radiation.

In spite of this uniform visual impression, the three coloring substances, described hereinafter, can be clearly distinguished with the aid of the checking device of the invention, also described hereinafter. Such distinguishing is effected by checking the fluorescing components of the Eu-doped additives, which have emissions in a very narrow red band. Since the emission spectra of the Eu-doped substances differ only with respect to the microstructure details of the spectra, the discrimination of the spectra is possible only with an extreme resolution. With a more superficial spectral examination, the presence of the red fluorescers can be determined, but distinguishing between the same is not possible.

EXAMPLE 1

For preparing 1 kg of die stamping ink, there can be used, alternatively, 75 g of any one of the following three substances (made by Riedel de Haen)
1. $Y_2O_3$: Eu ($Y_2O_3$ doped with Eu) or
2. $YVO_4$: Eu or
3. $La_2O_2S$: Eu.

A selected substance is mixed with 75 g of a broad-band luminous pigment, for example, $(Zn_xCd_{1-x})S$: Ag made by Riedel de Haen (commercial designation Flu Gründgelb 52016), and the two substances are mixed intimately, in a three-roller refiner, with

- 50 g of a yellow coloring pigment, for example, Pigmantgeld
- H 10 G extra (Azopigment), made by Farbwerke Hoechst
- 150 g of alkyd resin (Alkyldal U 63, made by Bayer Leverkusen)
- 20 g of a drying agent (Co-naphtenate, made by Borchers)
- 190 g of linseed oil
- 260 g of maleinate resin (for example, Syntholit M 100, made by Sunthopol Chemie, Buxtehude)
- 180 g of high-boiling mineral oil.

This provides a die stamping ink which can be used to die-stamp the paper and, thus, provide the paper with the substances protecting the paper against forgery.

EXAMPLE 2

If the fluorescers are not to be die-stamped or printed onto the paper, but rather incorporated directly into the paper, there may be used 100 g of a selected one of the following three substances:

$Y_2O_3$: Eu or
$YVO_4$: Eu or
$La_2O_2$: Eu as well as 100 g of a broad-band luminescent pigment, for example, $(Zn_xCd_{1-x})S$: Ag, in 20 l of $H_2O$ to form a 1% suspension.

This suspension is admixed with the pulp from which the paper is made, whereby a marking of the paper over the whole surface is obtained. With a dosing pump, this suspension is metered so as to obtain a final concentration of 0.1 to 1%, preferably, 0.5%, in the finished paper. If the paper is to be marked partially, the suspension is added to the still humid paper, at the provided locations, by dropping or spraying.

In principle, the most various combinations of these known substances may be used for the protection of papers against forgery in accordance with the invention. By checking the narrow bandedness, and/or the microstructure or details of the individual spectral regions, the identity of the respective dies can be proved also from the mixture of different substances. However, the fluorescence of one of these broad band substances cannot be distinguished visually from the mixture of this substance with one or several of the other substances.

The checking device of the present invention, described more fully hereinafter, aside from identifying the individual substances makes it possible also to distinguish perfectly the closely adjacent narrow band emissions. This is all the more true if the two narrow band substances, for example, $Y_2O_3$-Eu and $YVO_4$-Eu, are provided not in company with each other but at separate locations on the paper and are then checked separately.

Since the differences of the two narrow band fluorescences are materialized only by the non-fluorescent host lattices, a counterfeit of the spectra, without knowing exactly the composition of the substances, is possible only after a very extensive and costly series of trials. Consequently, while observing secrecy about the composition of the substances and using additional broad band camouflage substances, as well as narrow band substances which are not to be checked, a forgery is almost impossible.

The phenomenon of various substances fluorescing either in a broad band or in a narrow band is well established in the scientific literature. For example, in the publication LANDOLT-BÖRNSTEIN, published by Springer-Verlag, in 1967, the table on page 162 includes a die (909) which fluoresceses in a broad band in a red color. Page 193, 194, 195 and 197 of this publication illustrate dies exhibiting blue fluorescence in a broad band and their spectral lines. Attention is particulary directed to FIG. 11 on page 193, FIGS. 12, 13, 14 and 15 on page 194, FIGS. 16, 18 and 19 on page 195, and FIG. 23 on page 197.

In a publication by N. RIEHL, in 1966, there is an article by A. K. Levine & F. C. Palilla on pages 317 through 323 which clearly shows the difference between narrow band and broad band fluorescers. In particular, FIG. 3, on page 319, and FIG. 5 on page 21, each show two narrow band and two broad band fluorescent spectra of respective fluorescing substances. It can be readily recognized that distinctions can be determined between the two narrow band fluorescers. Thus, these narrow band fluorescers have characteristic emission spectra and the wave length, narrow bandedness and fine structure of the emission characteristics make it possible to infer what fluorescers have been used as well as their surrounding, mostly non-fluorescent host lattice, as is particularly clear from FIG. 4 on page 319 of this publication.

In the *Journal of Physical Chemistry* for 1969, Volume 30, pages 1483-1487 have an article by A. L. Harmer et al, on the fluorescence of $Nd^3$ in lithium yttrium fluoride, which shows that the change of the fine structure of narrow band elements, through host lattices, is well known in the art. In particular, this article establishes the change of the fine structure of emission lines for the element neodymium ($Nd^3$), embedded in yttrium or yttrium fluoride. Attention is particularly directed to FIG. 1 on page 1484 and FIG. 4 on page 1485.

It is thus well established that the emission spectra of broad band fluorescers and narrow band fluorescers can be readily determined inasmuch, more particularly, as narrow band fluorescers had characteristic emission spectra and the wave length, narrow bandedness and fine structure of the emission characteristics makes it possible to determine the used fluorescers and the surrounding, mostly non-fluorescent, host lattice. Furthermore, the change in the fine structure of narrow band elements, through host lattices, is also well established.

It is also known to imprint papers with various color-fluorescent inks so as to make it possible, in a reading operation, to check the papers for the presence or absence of a fluorescencers, for example, by means of suitable color filters. Such methods are shown, for example, in U.S. Pat. Nos. 3,473,027, 3,663,813, and 3,492,478. During the checking operation, the serial scanning of the areas of printing results in a train of signals corresponding to the imprinted code. The information represented by the substances fluorescing in different colors is concealed, with some certainty, at least from the persons not familiar with technique. This is particularly true in cases where, in this known method, colors are used which have the same visual appearance under visible light, or are invisible.

However, for a person skilled in the art, it is relatively easy to determined and imitate the fluorscences of the coded inks. That is, the sole requirement, in accordance with these known methods, which has been imposed on the fluorescent properties of inks, has been that the fluorescence emissions had to be narrow-banded and spaced apart to a sufficient extent such that the different colored fluorescent emissions can be distinguished from each other by means of the testing device. Because of these relatively modest requirements, a person skilled in the art is able to use a large number of commercially available substances of various chemical composition for imitating the inks and, consequently, a protection against forgery is out of the question.

Furthermore, and because of the modest requirements, the known testing devices may be tricked relatively easy also by forgeries comprising fluorescent substances of a different chemical composition, since, with these devices, in each case only a narrow range, at definite locations of the fluorescence spectrum, is checked for the presence of fluorescent. In these known testing devices, narrow-band fluorescent substances may be simulated even with organic colors which emit red or blue light in a broad band and which extend into the testing range only at one of their flanks, without detecting this circumstance. The checking devices may also be tricked if a false fluorescene emission is used having a band width so narrow that, for the next wave length, the photocells do not receive any light.

By contrast with the prior art arrangements, which, particularly in the case of Freeman et al U.S. Pat. No. 3,473,027 detect only the presence or absence of the florescing substances, the invention is based on the fact that many materials which fluoresce in a narrow band comprise an emissive microstructure or detailed spectrum structure which is characteristic for the specific chemical composition and which depends not only on the fluorescent elements of this substance but also on the structure of the non-fluorescent host lattice. Consequently, the exact chemical composition of the substance cannot be inferred from the emission spectra alone, so that an unrecognized imitation of the emissive microstructures, without knowing the exact manufacturing recipe, is made substantially more difficult, even for a specialist. This is true of the two examples mentioned above.

In addition, in accordance with the invention, fluorescent materials having emission spectra of different widths and colors are mixed together so that, with the naked eye, only the wide-band fluorescence is recognizable while a suitable designed checking device may detect all the details of the narrow-band fluorescence, both in the visible spectral range and in the invisible spectral range. Thus, the invention uses, for proving the authenticity of a paper, substances which, in the respective spectral range and upon a corresponding excitation, fluoresce in sharp, narrow-band emission lines.

To render the determination of the substances fluorescing in a narrow band more difficult, there are mixed therewith substances which fluoresce in a broad band and by means of which the impression of the narrow-band fluorescences, either visual or obtainable by simple auxiliary means of the measuring technique, is adulterated or complete changed. In such cases, the substances fluorescing in a broad band may emit light also outside the spectral ranges which are determinative for the authenticity test. This makes it possible, for example, to mask a substance producing, for example, red fluorescence in a narrow band with a substance producing, for example, green fluorescence in a broad band, to an extent such that the red substance can no longer be detected and determined except with a highly resolvent spectrophotometer while, with the naked eye, only a green color is recognizable.

For rendering the forgery still more difficult, a mixture of several substances producing fluorescence in a narrow band may advantageously be provided, and the mixture ratio may serve as an additional security. The security advantageously may be further increased by mixing the substances, used for the test of authenticity, with further fluorescent substances which emit in a narrow band outside the wave length range examined in the checking device. Thereby, the detection of the substances proving the authenticity is not effected. However, the work of a forger is made more difficult since it is very difficult for him to recognize which substances are evaluated in the authenticity test.

Thus, while testing papers for authenticity in accordance with the invention, not only the presence of the fluorescing red, orange, green or blue spectral components is checked, as is the case in the prior art, but, in addition, the narrowness of the band and the fine structure of the spectrum is also examined. To this end, in accordance with the invention, and with the aid of highly resolving spectrometers and depending on the requirements to be met, either only the narrowness of the band of the coarse spectral lines is checked, so that the location of the maxima of the spectral lines and, adjacent thereto to the right and left, the minima of the spectral lines are determined, or, if a greater accuracy is determined, with the finer resolution of the spectral lines, the emission line doublets are examined in a similar manner which also involves the checking of the fine structure of the spectral lines and, thereby, of the structure or nature of the used host lattice.

Since, in accordance with the invention, not only the fluorescers relevant for the authenticity tests are provided in the papers, and not only the presence of fluorescing substances at definite locations in the paper is determined, but also the exact structure of the determinative fluorescences is mechanically detected, the advantage is obtained that the features of authenticity which are determining for the test are still less recognizable and imitable by third persons than heretofore, but can be positively identified due to the exact evaluation of the fluorescences. Since the fluorescences are, preferably, incorporated into the paper already during the manufacture of the paper blank, rather than being imprinted as in the methods of the prior art, the localization of the substances is additionally rendered more difficult.

For providing the authenticity, it is further preferable for papers treated in accordance with the invention to use also, in the same manner as with known coded inks, chemical elements comprising elements of the rare earths. Particularly in connection with masking substances which fluoresce in the broad band, the strong narrow-band fluorescence of those elements proves very useful. As broad band fluoresces, there may be used dyes having emission spectra which extend both within and outside the narrow-band spectral regions used for checking the authenticities, such dyes being well known to those skilled in the art.

The device for checking the safety features, which, according to the invention, are provided in the paper, essentially comprises a transfer device, which moves the paper in its plane, a light source for illuminating the paper and thus exciting the fluorescent substance, a spectrophotometer for analyzing the radiation emitted by the paper, and an electronic circuit for evaluating the photocell currents to make a decision "good" or "no good" and to trigger subsequent operations resulting therefrom.

Figure 1:
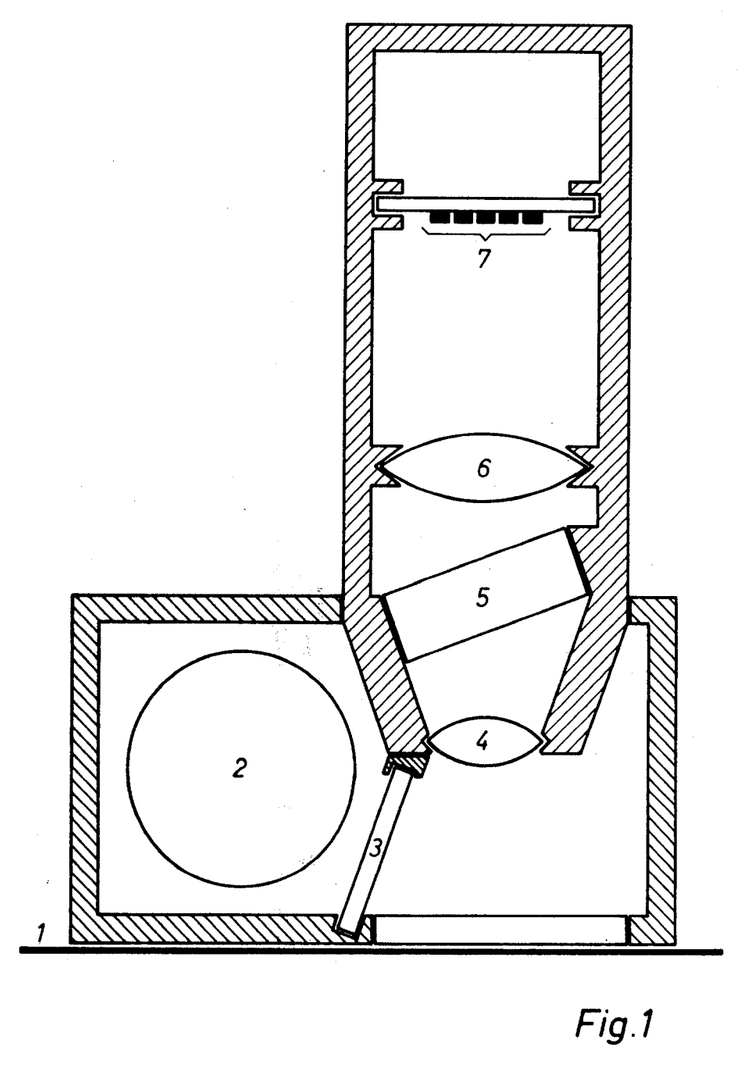
FIG. 1 is a schematic vertical sectional view of the checking device.

FIG. 1 shows schematically the structure of the checking device. The paper 1 is illuminated by a light source 2. Depending on the wavelength required to excite the fluorescent substances, the light source is a high- or low-pressure gas discharge lamp, a photo-flash lamp, or an incandescent lamp. However, the fluorescence may also be excited with an X-ray tube, an electron ray tube, or a radioactive substance. If optical fluorescence excitation is used, an optical filter 3 will be disposed between the light source and the paper in order to block interfering wave lengths in the light of the lamp.

The condenser lens 4 constitutes the light emitted by the fluorescent paper and focuses it on an inclined, narrow-band interference filter 5. In principle, of course, known highly resolving spectrophotometers may also be used as checking devices. However, with the inventive oblique arrangement of a narrow-band interference filter 5, as shown in FIG. 1, instead of the usual gratings or prisms, a substantially more compacted structure of the checking device is obtained. In the device shown in the drawing, the length of the optical path is about 2 cm while known spectrometers having the same resolution require an optical path of 20 to 50 cm. In addition, due to the mounting of additional constructional elements in the optical axis, without deflected ray paths, the device is substantially less expensive in manufacture.

As is well known, the wave lengths of the maximum transmission of an interference filter is dependent on the incidence angle of the light. The more oblique the light is incident, the more the wave lengths of the passed light are shifted. The lens 6 focuses the passed light on an arrangement of like photocells 7 in the focal plane of lens 6. Each of the photocells is struck by monochromatic light only. Thus, each of the photocells measures the fluorescence of the paper at a different wave length.

Since the photocells 7 are disposed exactly at the locations where the maxima or minima of intensity of quite definite wave lengths have to appear, the device can be adjusted to the fluorescer to be checked by a simple displacement of the photocells in the roll.

Figure 2:
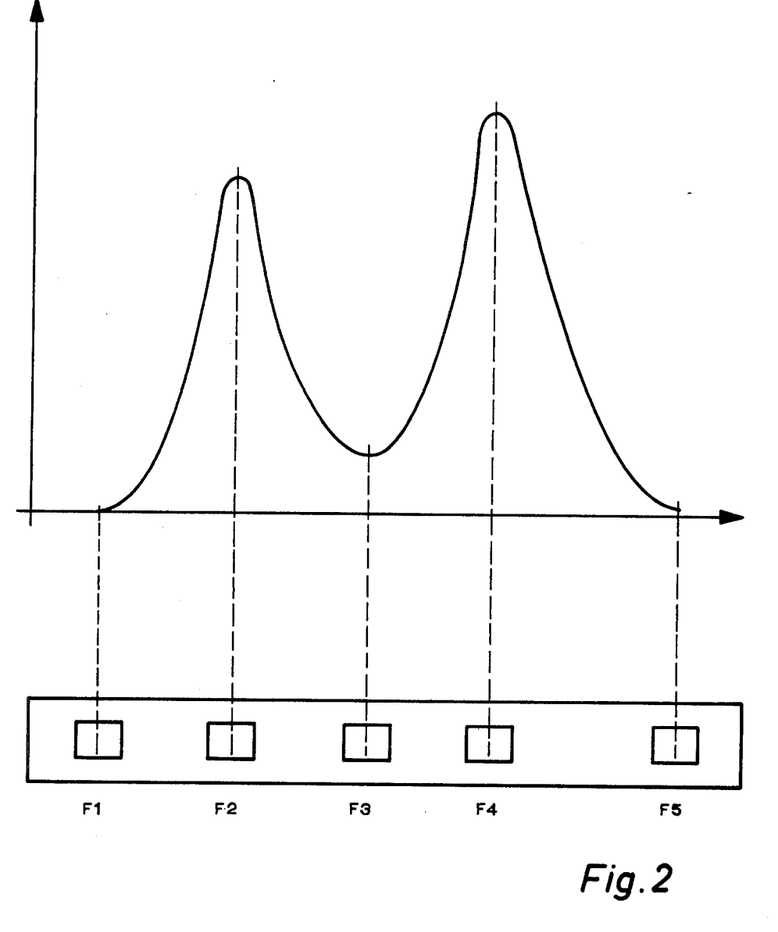
FIG. 2 shows the geometric arrangement of the scanning photocells for the identification of the emission-line doublets.

FIG. 2 shows the geometric arrangement of the photocells which is appropriately chosen in order to identify an emission-line doublet. In this arrangement, the photocells F2 and F4 measures the light emission at the wave-lengths of the intensity maxima, while the photocells F1, F3, and F5 measure the brightness of the background. Thus, if a paper contains a substance having an emission spectrum as shown in FIG. 2, the photocells F2 and F4 will provide strong signals, while the photocells F1, F3 and F5 will provide no signals.

Figure 3:
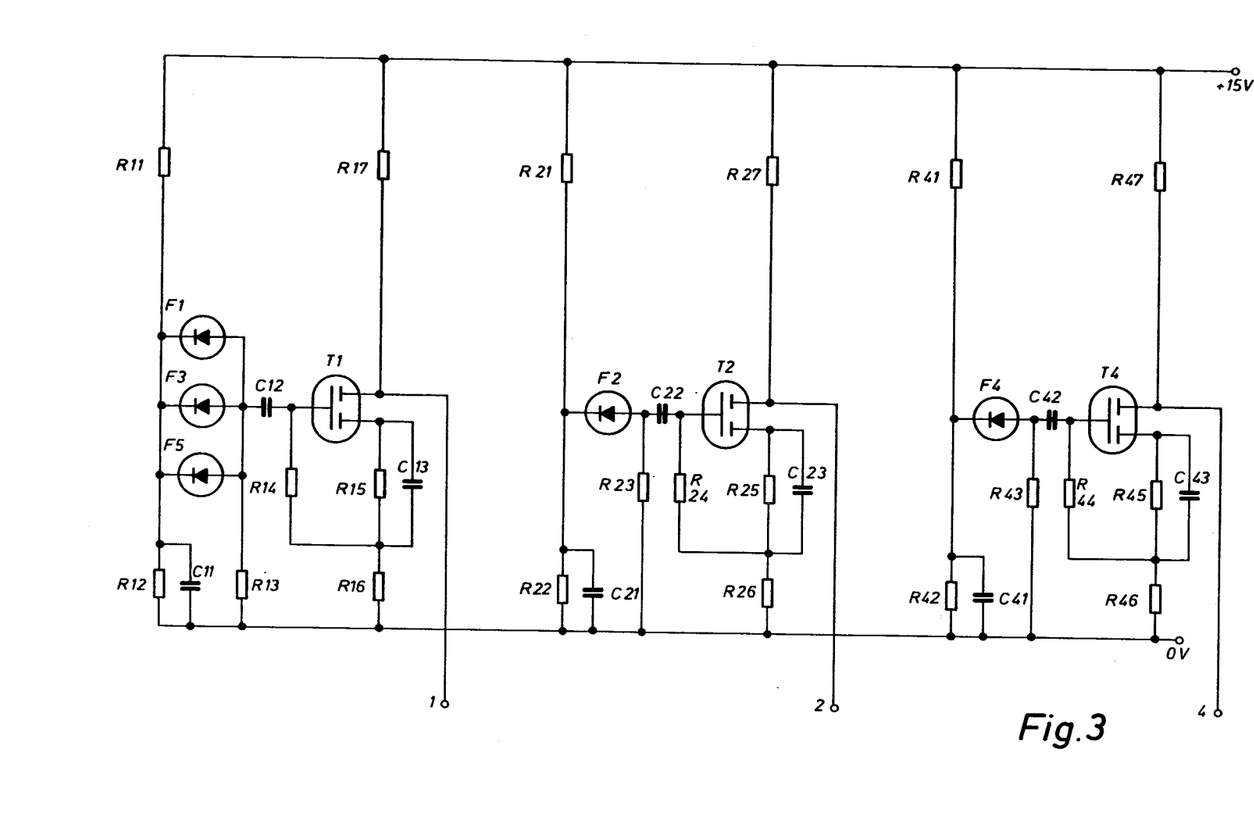
FIG. 3 is a schematic wiring diagram of the amplifier circuits for the amplification of the photocell currents.
Figure 4:
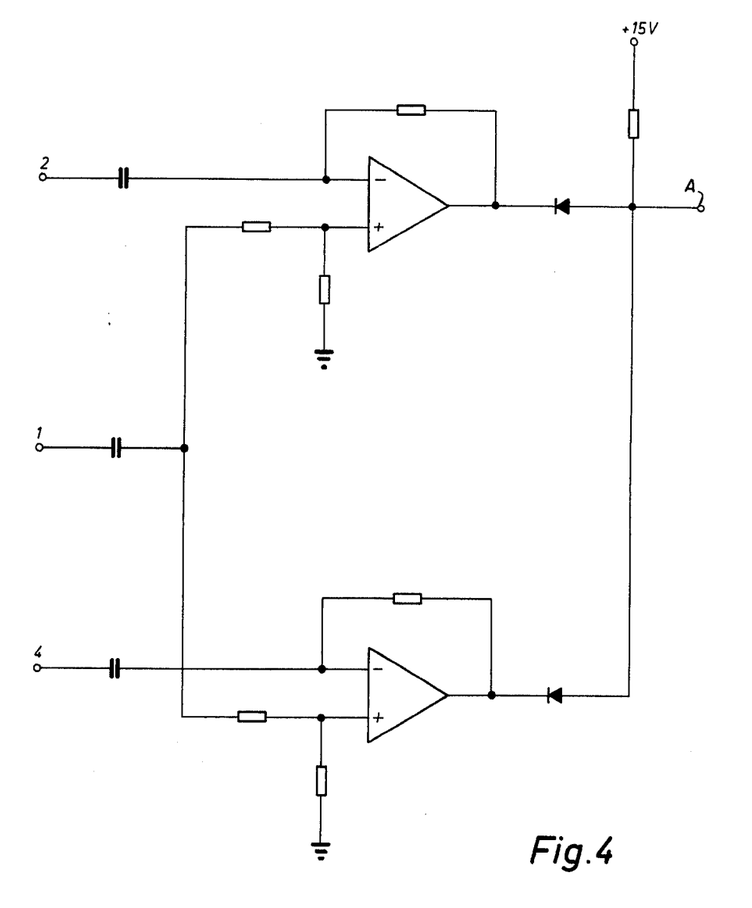
FIG. 4 is a schematic wiring diagram illustrating circuitry for the formation of the difference between two photocell currents.

The electronic evaluation of the signals is shown in FIGS. 3 and 4.

In the preamplifier (FIG. 3), the photocurrents of the five photocells are amplified by means of field-effect transistors. In order to save on components, the photocurrents of the photocells F1, F3 and F5 are added together and amplified jointly.

In the comparator (FIG. 4), the difference between the photocurrents from the photocells F2 and F4 and the photocurrents from F1, F3, and F5 is formed with differential amplifiers. Thus, it is checked whether the two intensity maxima of FIG. 2 stand out from the background. If that is the case, a positive voltage surge is obtained at the output A of the comparator. This output signal can be processed, in known manner, to control relays or generate audible or visual signals.

The subtraction has the added advantage that fluorescent substances which emit light within broad bands and are added to substances emitting light within narrow bands to increase the safety against forgery do not influence the identification of the latter substances because the additional substances generate, in all photocells, only additional, approximately equal photocurrents which are eliminated during the subtraction.

Figure 5:
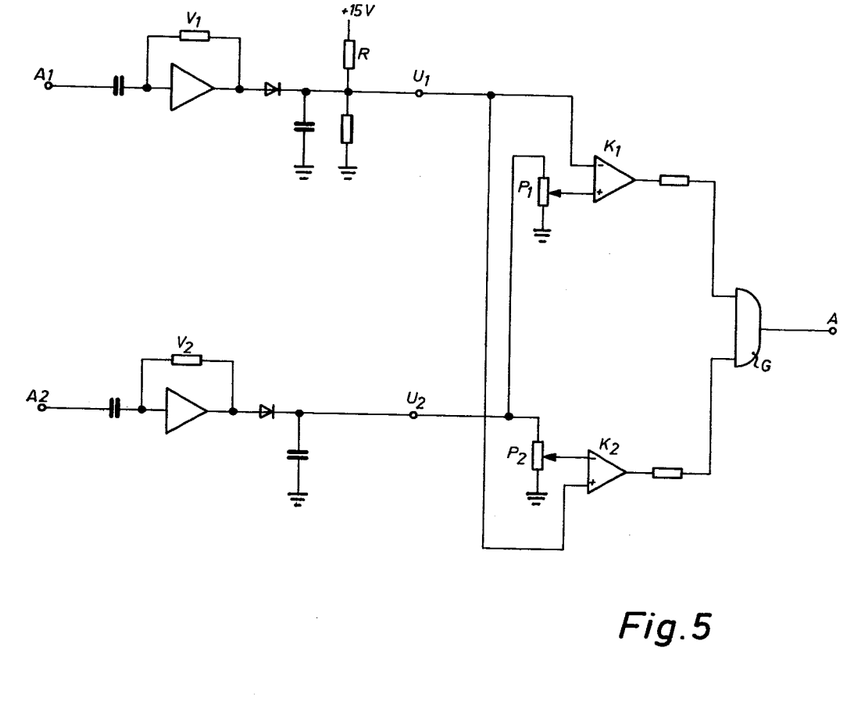
FIG. 5 is a view similar to FIG. 4 illustrating the circuitry for the formation of the quotient of two photocell currents.

FIG. 5 shows a simple circuit with which not the difference but the quotient between the photocurrents of two photocells is compared to definite maximum and minimum values and used to establish the authenticity of the paper. The circuit has the advantage of affording increased safety because dirt on the paper, variations in the brightness of the lamp, and an inaccurate position of the paper in the checking device do not affect the measuring accuracy.

To permit the use of a.c. amplifiers, a light source with periodic changes of brightness is employed. In the two photocells, this results in alternating currents whose amplitudes are proportional to the fluorescence at the light wave lengths being examined (steady radiation can be processed in the same circuit with slightly more complicated d.c. amplifiers). The photocurrents of the two photocells are applied via the terminals A1 and A2 to the amplifiers V1 and V2, respectively, are amplified, then rectified, and applied to the comparators $K_1$ and $K_2$. At the potentiometers $P_1$ and $P_2$, the permissible maximum and minimum values of the quotient between the two photocurrents are adjusted.

For a better understanding of the formation of the quotient, the voltage-dividing ratio of the two potentiometers is designated $K_1$ and $K_2$, respectively, and the voltages behind the rectifiers, which voltage are caused by the photocurrents, are denoted by $U_1$ and $U_2$, If $$U_1 < k_1 \cdot U_2,$$

and $$U_1 > k_2 \cdot U_2,$$

a positive voltage is obtained at the outputs of both comparators and thus also at the output of the AND-gate G. The above relationship can also be written as $$k_2 (U_1/U_2) < k_1.$$

Thus, a positive output signal is obtained only if the quotient of the two photocurrents lies within a tolerance which is characteristic of the paper. If no light is incident on the photocells, the voltages $U_1$ and $U_2$ are zero. In this case, the high-value registor R insures a small zero shift of $U_1$, which prevents the output signal "good" from occurring in a checking apparatus without a paper.

In an analogous manner, it is possible to evaluate signals from photocell arrangements which measure two or more spectral lines.

Interference filters are commercially available which have a half-value width of 1.5 Å. With such filters, up to 10 emission lines can be separated from each other. The device described above permits the emission of the fluorescent substance to be checked only within a relatively narrow spectral range because the dispersion element is an interference filter. For checking substances whose analysis requires a wider spectral range, the same device may, of course, be used if the interference filter is replaced by a dispersion prism or a dispersion grating. Such optical arrangements are commonly used in spectroscopes or spectrophotometers. If dispersion prisms or diffraction gratings are used, the spectral analysis can be carried out in the above-described arrangement with several photocells simultaneously and also without any moving parts.

While specific embodiments of the invention have been shown and described in detail to illustrate the application of the principles of the invention, it will be understood that the invention may be embodied otherwise without departing from such principles.

What is claimed is:

1. A device for checking the emission spectra in papers secured against forgery by containing, at at least one point, safety features in the form of fluorescent materials of a particular concentration which, in the excited condition, fluoresce, in at least one of the visible, ultraviolet and infrared spectral ranges, in characteristic emission spectra, and in which the fluorescent materials are constituted by rare earth elements embedded in substantially non-fluorescening crystal host lattices, and which, in the selected spectral range, fluoresce, in spectrally very narrow and sharp emission lines, determinable only by a high resolution spectrophotometer, so that the chemical structure of the fluorescent materials can be determined by using high resolution spectrophotometry to detect the wave-lengths at which the maxima very narrow and sharp emission lines are present, and to detect the wavelength at which the minima of the emission lines are present to detect the flanks of the emission lines; said device comprising, in combination, an excitation light source for exciting the fluorescent materials to emit such characteristic emission spectra; a dispersion element, in the path of the rays of the emitted characteristic spectra, operable to fan out th characteristic emission spectra of the fluorescent substances; a photoelectric receiving unit, on which the fanned-out emission spectra is projected; said photoelectric receiving unit including, with respect to each maxima and each minima of the emission lines to be detected, at least one respective photoelectric transducer so geometrically located with respect to the fanned-out emission spectra as to be responsive to the associated emission lines to produce an output corresponding to the detected emission lines; and an evaluation unit connected to said photoelectric transducers and operable for comparing the emission values detected by said photoelectric receiving unit with predetermined desired values for checking the authenticity of papers subjected to scanning by the high resolution spectrophotometer constituted by said light source, said dispersion element, said receiving unit and said evaluation unit.

2. A device, as claimed in claim 1, including means in said evaluation unit operable to derive the quotient values between the maxima and minima as measured values, and voltage dividers operable to adjust the permissible tolerance for the quotient value.

3. A device, as claimed in claim 1, including means in said evaluation unit operable to derive the difference values between the maxima and the minima as measured values.

4. A device, as claimed in claim 1, in which said dispersion element is a narrow band interference filter.

5. In a paper secured against forgery containing, at at least one point, safety features in the form of fluorescent materials of a particular concentration which, in the excited condition, fluoresce in at least one selected spectral range of the visible, ultraviolet and infrared spectral ranges; an improvement comprising said fluorescent materials being constituted by rare earth elements embedded in substantially non-fluorescing crystal host lattices which are contained at the at least one point of the paper, said rare earth elements fluorescing in the at least one selected spectral range in very narrow and sharp emission lines having maxima and minima flanking the maxima and determinable only by a high resolution spectrophotometer, details of said lines in the at least one selected spectral range being characteristic of the crystal host lattice structure, so that the chemical structure of the fluorescent materials can be determined by using high resulution spectrophotometry to detect the wave lengths at which the maxima of the very narrow and sharp emission lines are present, and detect the wave length at which the minima of the emission lines are present to detect the flanks of the emission lines; whereby said paper can be differentiated by instrumentation testing from so-called impression forgeries.

6. A paper according to claim 5 wherein said rare earth elements embedded in substantially non-fluorescing crystal host lattices comprise at least one of the group consisting of, $Y_2O_3$: Eu, $YVO_4$: Eu, $La_2O_2S$: Eu, and $La_2O_2$: Eu.

7. A paper according to claim 5, in which the materials affording safety are mixed with additional materials which fluoresce within narrow wavebands but which are not evaluated in an authenticity check.

8. A paper according to claim 5, which contains materials, fluorescing within a narrow spectral band, at points which are not evaluated in an authenticity check.

9. A method of preventing forgery in a paper comprising, incorporating a fluorescent material at at least one point on the paper which includes a rare earth element which fluoresces in at least one selected spectral range of the visible, ultraviolet and infrared spectral ranges, the rare earth element embeded in a substantially non-fluorescing crystal host lattice, the rare earth fluorescing in very narrow and sharp emission lines having maxima and minima flanking the maxima at known wave lengths; detecting the presence of said maxima; and detecting the presence of said minima; whereby the absence of one of said maxima and minima indicates the presence of a forged paper not having the incorporated rare earth in its crystal host lattice.

* * * * *